(12) United States Patent
Kemp et al.

(10) Patent No.: US 9,398,940 B2
(45) Date of Patent: *Jul. 26, 2016

(54) ORAL CARE IMPLEMENT WITH CAVITATION SYSTEM

(71) Applicant: COLGATE-PALMOLIVE COMPANY, New York, NY (US)

(72) Inventors: James Herbert Kemp, Basking Ridge, NJ (US); Malcolm Williams, Piscataway, NJ (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 117 days.

This patent is subject to a terminal disclaimer.

(21) Appl. No.: 14/293,582

(22) Filed: Jun. 2, 2014

(65) Prior Publication Data
US 2014/0259471 A1    Sep. 18, 2014

Related U.S. Application Data

(63) Continuation of application No. 12/159,279, filed as application No. PCT/US2008/065704 on Jun. 4, 2008, now Pat. No. 8,747,005.

(51) Int. Cl.
| | |
|---|---|
| *A61C 17/34* | (2006.01) |
| *A61C 17/20* | (2006.01) |
| *A61K 8/11* | (2006.01) |
| *A61K 8/22* | (2006.01) |

(Continued)

(52) U.S. Cl.
CPC .............. *A61C 17/3481* (2013.01); *A61C 17/20* (2013.01); *A61K 8/11* (2013.01); *A61K 8/22* (2013.01); *A61K 8/347* (2013.01); *A61Q 11/00* (2013.01); *A46B 13/023* (2013.01); *A46B 15/0016* (2013.01); *A46B 2200/1066* (2013.01)

(58) Field of Classification Search
CPC ............. A61C 17/3481; A46B 13/023; A46B 15/0016
USPC .......................... 15/167.1, 22.1; 401/132, 268
See application file for complete search history.

(56) References Cited

U.S. PATENT DOCUMENTS

| | | | |
|---|---|---|---|
| 3,636,947 | A | 1/1972 | Balamuth |
| 3,800,782 | A | 4/1974 | Josephson et al. |

(Continued)

FOREIGN PATENT DOCUMENTS

| | | |
|---|---|---|
| EP | 0785737 | 7/1997 |
| EP | 0821896 | 2/1998 |

(Continued)

OTHER PUBLICATIONS

International Search Report and the Written Opinion of the International Searching Authority issued in International Application PCT/US2008/065704 mailed Apr. 15, 2009.

*Primary Examiner* — Mark A Laurenzi
*Assistant Examiner* — Bradley Oliver (57) ABSTRACT

An oral care implement generates cavitation within the oral cavity. One or more cavitation cleaning elements may be located in the head area of the oral care implement. The cavitation cleaning element vibrates at a frequency that produces cavitation of fluids within the oral cavity. The oral care implement may include an elastomeric cavitation cleaning element. A cleaning element may be configured to vibratory release an oral care substance from a container; and a body for gripping the implement.

12 Claims, 7 Drawing Sheets

(51) Int. Cl.
*A61K 8/34* (2006.01)
*A61Q 11/00* (2006.01)
*A46B 15/00* (2006.01)
*A46B 13/02* (2006.01)

(56) References Cited

U.S. PATENT DOCUMENTS

| | | |
|---|---|---|
| 3,840,932 A | 10/1974 | Balamuth |
| 3,943,914 A | 3/1976 | Grenfell et al. |
| 3,957,964 A | 5/1976 | Grimm |
| 4,043,042 A | 8/1977 | Perfect |
| 4,071,956 A | 2/1978 | Andress |
| 4,148,309 A | 4/1979 | Beibel |
| 4,197,855 A | 4/1980 | Lewin |
| 4,236,510 A | 12/1980 | Hatter et al. |
| 4,303,077 A | 12/1981 | Lewin et al. |
| 4,310,002 A | 1/1982 | Takinishi et al. |
| 4,348,378 A | 9/1982 | Kosti |
| 4,470,810 A | 9/1984 | Bourdeau et al. |
| 4,488,873 A | 12/1984 | Bloomfield et al. |
| 4,500,294 A | 2/1985 | Lewis |
| 4,564,355 A | 1/1986 | Traiger et al. |
| 4,592,727 A | 6/1986 | Bloomfield |
| 4,697,601 A | 10/1987 | Durkee et al. |
| 4,764,378 A | 8/1988 | Keith et al. |
| 4,787,847 A | 11/1988 | Martin et al. |
| 4,952,143 A | 8/1990 | Becker et al. |
| 4,976,618 A | 12/1990 | Anderson |
| 4,983,381 A | 1/1991 | Torres Zaragoza |
| 4,995,404 A | 2/1991 | Nemir |
| 5,013,553 A | 5/1991 | Southard et al. |
| 5,074,786 A | 12/1991 | Woodward |
| 5,112,616 A | 5/1992 | McCarty |
| 5,119,831 A | 6/1992 | Robin et al. |
| 5,138,733 A | 8/1992 | Bock |
| 5,162,037 A | 11/1992 | Whitson-Fischman |
| 5,176,151 A | 1/1993 | Harding |
| 5,212,476 A | 5/1993 | Maloney |
| 5,223,259 A | 6/1993 | Lackney |
| 5,288,497 A | 2/1994 | Stanley et al. |
| 5,288,498 A | 2/1994 | Stanley et al. |
| 5,298,256 A | 3/1994 | Flockhart et al. |
| 5,309,590 A | 5/1994 | Guiliani et al. |
| 5,330,357 A | 7/1994 | Keller |
| 5,361,506 A | 11/1994 | Beeuwkes, III |
| 5,369,831 A | 12/1994 | Bock |
| 5,387,598 A | 2/1995 | Rossignol |
| 5,440,393 A | 8/1995 | Wenz |
| 5,460,527 A | 10/1995 | Kittelsen |
| 5,476,384 A | 12/1995 | Guiliani et al. |
| 5,520,924 A | 5/1996 | Chapman et al. |
| 5,562,449 A | 10/1996 | Jacobs et al. |
| 5,643,204 A | 7/1997 | Cover |
| 5,650,192 A | 7/1997 | Britton et al. |
| 5,650,284 A | 7/1997 | Erlanger et al. |
| 5,700,449 A | 12/1997 | Katayama |
| 5,707,353 A | 1/1998 | Mazer et al. |
| 5,759,159 A | 6/1998 | Masreliez |
| 5,762,494 A | 6/1998 | Archambault |
| 5,770,182 A | 6/1998 | Fischer |
| 5,795,153 A | 8/1998 | Rechmann |
| 5,824,334 A | 10/1998 | Stanley et al. |
| 5,842,860 A | 12/1998 | Funt |
| 5,860,942 A | 1/1999 | Cox |
| 5,874,677 A | 2/1999 | Bab et al. |
| 5,875,798 A | 3/1999 | Petrus |
| 5,885,611 A | 3/1999 | Church et al. |
| 5,888,534 A | 3/1999 | El-Rashidy et al. |
| 5,894,620 A | 4/1999 | Polaert et al. |
| 5,928,187 A | 7/1999 | Glukhov et al. |
| 5,939,049 A | 8/1999 | Miller et al. |
| 5,944,519 A | 8/1999 | Griffiths |
| 5,954,673 A | 9/1999 | Staehlin et al. |
| 5,981,591 A | 11/1999 | Deihl |
| 5,993,413 A | 11/1999 | Aaltonen et al. |
| 6,049,934 A | 4/2000 | Discko |
| 6,056,548 A | 5/2000 | Neuberger et al. |
| 6,085,379 A | 7/2000 | Stafford |
| 6,090,053 A | 7/2000 | Ruetschi et al. |
| 6,108,850 A | 8/2000 | McLaughlin |
| 6,112,356 A | 9/2000 | Hashey |
| 6,135,126 A | 10/2000 | Joshi |
| 6,135,774 A | 10/2000 | Hack et al. |
| 6,139,319 A | 10/2000 | Sauer et al. |
| 6,142,694 A | 11/2000 | Rivlin et al. |
| 6,177,097 B1 | 1/2001 | Hanke |
| 6,180,682 B1 | 1/2001 | Place |
| 6,186,780 B1 | 2/2001 | Hibst et al. |
| 6,200,550 B1 | 3/2001 | Masterson et al. |
| 6,203,320 B1 | 3/2001 | Williams et al. |
| 6,213,662 B1 | 4/2001 | Aljanedi |
| 6,213,663 B1 | 4/2001 | Micaletti et al. |
| 6,221,031 B1 | 4/2001 | Heraud |
| 6,221,392 B1 | 4/2001 | Khankari et al. |
| 6,231,338 B1 | 5/2001 | de Josselin de Jong et al. |
| 6,238,118 B1 | 5/2001 | Tryon |
| 6,264,974 B1 | 7/2001 | Madhat |
| 6,280,394 B1 | 8/2001 | Maloney et al. |
| RE37,382 E | 9/2001 | Yates |
| 6,284,262 B1 | 9/2001 | Place |
| 6,326,022 B1 | 12/2001 | Katz |
| 6,331,088 B2 | 12/2001 | Owens |
| 6,345,629 B1 | 2/2002 | Vives |
| 6,387,392 B1 | 5/2002 | Saito et al. |
| 6,397,859 B1 | 6/2002 | Byrd |
| 6,413,541 B1 | 7/2002 | Shirai et al. |
| 6,434,773 B1 | 8/2002 | Kuo |
| 6,435,873 B1 | 8/2002 | Burgio |
| 6,482,008 B2 | 11/2002 | Perdomini et al. |
| 6,503,222 B2 | 1/2003 | Lo |
| 6,503,486 B2 | 1/2003 | Xu |
| 6,514,483 B2 | 2/2003 | Xu |
| 6,589,562 B1 | 7/2003 | Shefer et al. |
| 6,607,387 B2 | 8/2003 | Mault |
| 6,613,001 B1 | 9/2003 | Dworkin |
| 6,634,051 B1 | 10/2003 | Dragan et al. |
| 6,644,878 B2 | 11/2003 | Hall et al. |
| 6,647,549 B2 | 11/2003 | McDevitt et al. |
| 6,648,641 B1 | 11/2003 | Viltro et al. |
| 6,685,375 B1 | 2/2004 | Crocker |
| 6,689,078 B1 | 2/2004 | Rehkemper et al. |
| 6,721,987 B2 | 4/2004 | McDevitt et al. |
| 6,729,789 B2 | 5/2004 | Gordon |
| 6,730,316 B2 | 5/2004 | Chen |
| 6,733,791 B2 | 5/2004 | Mann et al. |
| 6,735,803 B2 | 5/2004 | Kuo |
| 6,736,776 B2 | 5/2004 | Miles |
| 6,743,443 B1 | 6/2004 | Furitsu et al. |
| 6,766,824 B2 | 7/2004 | Taylor |
| 6,786,092 B2 | 9/2004 | Nakao |
| 6,827,910 B2 | 12/2004 | Chen |
| 6,832,913 B2 | 12/2004 | Lehmann |
| 6,860,736 B2 | 3/2005 | Allred et al. |
| 6,860,879 B2 | 3/2005 | Irion et al. |
| 6,866,509 B2 | 3/2005 | Jensen |
| 6,872,405 B2 | 3/2005 | Takaishi et al. |
| 6,916,287 B2 | 7/2005 | Dematteis et al. |
| 6,932,978 B2 | 8/2005 | Huntley |
| 6,944,903 B2 | 9/2005 | Gavney, Jr. |
| 6,948,875 B1 | 9/2005 | Jang |
| 6,955,538 B1 | 10/2005 | Borch et al. |
| 7,011,644 B1 | 3/2006 | Andrew et al. |
| 7,025,983 B2 | 4/2006 | Leung et al. |
| 7,059,853 B2 | 6/2006 | Hegemann |
| 7,077,812 B2 | 7/2006 | Naghavi |
| 7,080,980 B2 | 7/2006 | Klupt |
| 7,118,376 B2 | 10/2006 | Jodaikin et al. |
| 7,128,899 B2 | 10/2006 | Chen |
| 7,128,964 B2 | 10/2006 | Kaya et al. |
| 7,144,247 B2 | 12/2006 | Black |
| 7,156,656 B2 | 1/2007 | Duret |
| 7,182,542 B2 | 2/2007 | Hohlbein |
| 7,296,318 B2 | 11/2007 | Mourad et al. |
| 8,171,591 B2 | 5/2012 | Hall et al. |

(56) References Cited

U.S. PATENT DOCUMENTS

| | | |
|---|---|---|
| 2001/0000205 A1 | 4/2001 | Hague et al. |
| 2001/0002228 A1 | 5/2001 | Owens |
| 2001/0003147 A1 | 6/2001 | Yokoyama et al. |
| 2001/0046511 A1 | 11/2001 | Zerbe et al. |
| 2002/0018800 A1 | 2/2002 | Pinney et al. |
| 2002/0044817 A1 | 4/2002 | Hall et al. |
| 2002/0071857 A1 | 6/2002 | Kararli et al. |
| 2002/0081138 A1 | 6/2002 | Hall et al. |
| 2002/0088068 A1* | 7/2002 | Levy .............. A46B 15/0002 15/22.1 |
| 2002/0090252 A1 | 7/2002 | Hall et al. |
| 2002/0114658 A1 | 8/2002 | Allen et al. |
| 2002/0143276 A1 | 10/2002 | Ernst |
| 2002/0152565 A1 | 10/2002 | Klupt |
| 2003/0003421 A1 | 1/2003 | Bestenheider et al. |
| 2003/0056307 A1 | 3/2003 | Tybinkowski et al. |
| 2003/0068378 A1 | 4/2003 | Chen et al. |
| 2003/0095828 A1 | 5/2003 | Hofstedt |
| 2003/0116197 A1 | 6/2003 | Taylor |
| 2003/0118653 A1 | 6/2003 | Chen et al. |
| 2003/0158206 A1 | 8/2003 | Billotte et al. |
| 2003/0186191 A1 | 10/2003 | Lawter et al. |
| 2003/0194678 A1 | 10/2003 | Viltro et al. |
| 2003/0198503 A1 | 10/2003 | Gordon |
| 2003/0198580 A1 | 10/2003 | Chen |
| 2003/0211440 A1 | 11/2003 | Kuo et al. |
| 2004/0013612 A1 | 1/2004 | Oxman et al. |
| 2004/0022576 A1 | 2/2004 | Hoyle et al. |
| 2004/0028456 A1 | 2/2004 | Giraldo |
| 2004/0030224 A1 | 2/2004 | Sotos et al. |
| 2004/0031114 A1 | 2/2004 | Dragan et al. |
| 2004/0062591 A1 | 4/2004 | Hall et al. |
| 2004/0062806 A1 | 4/2004 | Martini et al. |
| 2004/0091834 A1 | 5/2004 | Rizoiu et al. |
| 2004/0096803 A1 | 5/2004 | Huang et al. |
| 2004/0141799 A1 | 7/2004 | Jackow |
| 2004/0146831 A1 | 7/2004 | Balmelli et al. |
| 2004/0245675 A1 | 12/2004 | Clarke et al. |
| 2005/0002726 A1 | 1/2005 | Bostal |
| 2005/0025719 A1 | 2/2005 | Nussen |
| 2005/0037316 A1 | 2/2005 | Sholder |
| 2005/0053665 A1 | 3/2005 | Ek et al. |
| 2005/0058609 A1 | 3/2005 | Nazeri |
| 2005/0060822 A1 | 3/2005 | Chenvainu |
| 2005/0069372 A1 | 3/2005 | Hohlbein et al. |
| 2005/0107849 A1 | 5/2005 | Altshuler et al. |
| 2005/0170316 A1 | 8/2005 | Russell et al. |
| 2005/0238412 A1 | 10/2005 | Jacobs et al. |
| 2005/0255424 A1 | 11/2005 | Hack et al. |
| 2006/0003284 A1 | 1/2006 | Sale et al. |
| 2006/0019214 A1 | 1/2006 | Lawrence et al. |
| 2006/0021165 A1 | 2/2006 | Boland et al. |
| 2006/0042650 A1 | 3/2006 | Ochs |
| 2006/0057087 A1 | 3/2006 | Moskovich et al. |
| 2006/0078589 A1 | 4/2006 | Jensen et al. |
| 2006/0084026 A1 | 4/2006 | Cinader et al. |
| 2006/0084036 A1 | 4/2006 | Boston |
| 2006/0141421 A1 | 6/2006 | Braunecker et al. |
| 2006/0191086 A1 | 8/2006 | Mourad |
| 2006/0239532 A1 | 10/2006 | Taguchi et al. |
| 2007/0000514 A1 | 1/2007 | O'Shaughnessey et al. |
| 2007/0003906 A1 | 1/2007 | Anderson |
| 2007/0015112 A1 | 1/2007 | Hochman et al. |
| 2007/0031785 A1 | 2/2007 | Whalen |
| 2007/0104659 A1 | 5/2007 | Yasuda |
| 2007/0113374 A1 | 5/2007 | Joshi |
| 2007/0124177 A1 | 5/2007 | Engleson et al. |
| 2008/0052848 A1 | 3/2008 | Hohlbein |

FOREIGN PATENT DOCUMENTS

| | | |
|---|---|---|
| EP | 0852136 | 7/1998 |
| EP | 0903115 | 3/1999 |
| EP | 0933044 | 8/1999 |
| EP | 0942670 | 9/1999 |
| EP | 0959718 | 12/1999 |
| EP | 1018908 | 7/2000 |
| EP | 1023856 | 8/2000 |
| EP | 1038469 | 9/2000 |
| EP | 1079711 | 3/2001 |
| EP | 1113736 | 7/2001 |
| EP | 1143876 | 10/2001 |
| EP | 1147746 | 10/2001 |
| EP | 1164891 | 1/2002 |
| EP | 1190643 | 3/2002 |
| EP | 1197163 | 4/2002 |
| EP | 1259186 | 11/2002 |
| EP | 1307159 | 5/2003 |
| EP | 1335678 | 8/2003 |
| EP | 1335679 | 8/2003 |
| EP | 1458302 | 9/2004 |
| EP | 1505922 | 2/2005 |
| EP | 1506726 | 2/2005 |
| EP | 1543795 | 6/2005 |
| EP | 1545263 | 6/2005 |
| EP | 1547542 | 6/2005 |
| EP | 1575398 | 9/2005 |
| EP | 1575448 | 9/2005 |
| EP | 1578227 | 9/2005 |
| EP | 1608287 | 12/2005 |
| EP | 1639913 | 3/2006 |
| EP | 1641605 | 4/2006 |
| EP | 1670380 | 6/2006 |
| EP | 1694238 | 8/2006 |
| EP | 1729716 | 12/2006 |
| EP | 1734888 | 12/2006 |
| EP | 1755479 | 2/2007 |
| EP | 1761200 | 3/2007 |
| EP | 1765215 | 3/2007 |
| EP | 1765216 | 3/2007 |
| EP | 1781188 | 5/2007 |
| GB | 2401795 | 11/2004 |
| JP | H8-169811 A | 7/1996 |
| JP | 2000-225023 A | 8/2000 |
| JP | 2000-300349 A | 10/2000 |
| JP | 2001-008735 A | 1/2001 |
| JP | 2001-057908 A | 3/2001 |
| JP | 2001-190332 A | 7/2001 |
| JP | 2001-238730 A | 9/2001 |
| JP | 2002-000623 A | 1/2002 |
| JP | 2002-101956 A | 4/2002 |
| JP | 2002-142865 A | 5/2002 |
| JP | 2003-009952 A | 1/2003 |
| JP | 2003-019033 A | 1/2003 |
| JP | 2003-052458 A | 2/2003 |
| JP | 2003-169716 A | 6/2003 |
| JP | 2003-174934 A | 6/2003 |
| JP | 2003-289946 A | 10/2003 |
| JP | 2003-304933 A | 10/2003 |
| JP | 2004-174158 A | 6/2004 |
| JP | 2004-242985 A | 9/2004 |
| JP | 2004-344264 A | 12/2004 |
| JP | 2005-013375 A | 1/2005 |
| JP | 2005-058768 A | 3/2005 |
| JP | 2005-065827 A | 3/2005 |
| JP | 2005-110829 A | 4/2005 |
| JP | 2005-118191 A | 5/2005 |
| JP | 2005-185410 A | 7/2005 |
| JP | 2006-061486 A | 3/2006 |
| RU | 2359595 | 6/2009 |
| RU | 2397734 | 8/2010 |
| WO | WO 92/15198 | 9/1992 |
| WO | WO 98/56277 | 12/1998 |
| WO | WO 00/15076 | 3/2000 |
| WO | WO 00/41645 | 7/2000 |
| WO | WO 00/53053 | 9/2000 |
| WO | WO 01/62177 | 8/2001 |
| WO | WO 01/93721 | 12/2001 |
| WO | WO 02/15736 | 2/2002 |
| WO | WO 02/19867 | 3/2002 |
| WO | WO 02/24025 | 3/2002 |
| WO | WO 02/26079 | 4/2002 |
| WO | WO 02/41801 | 5/2002 |

(56) References Cited

FOREIGN PATENT DOCUMENTS

| | | |
|---|---|---|
| WO | WO 02/41802 | 5/2002 |
| WO | WO 02/058508 | 8/2002 |
| WO | WO 02/063994 | 8/2002 |
| WO | WO 02/071894 | 9/2002 |
| WO | WO 03/053271 | 7/2003 |
| WO | WO 03/082047 | 10/2003 |
| WO | WO 03/096923 | 11/2003 |
| WO | WO 03/103985 | 12/2003 |
| WO | WO 2004/021914 | 3/2004 |
| WO | WO 2004/028292 | 4/2004 |
| WO | WO 2004/047588 | 6/2004 |
| WO | WO 2004/054403 | 7/2004 |
| WO | WO 2004/056287 | 7/2004 |
| WO | WO 2004/087002 | 10/2004 |
| WO | WO 2004/091341 | 10/2004 |
| WO | WO 2005/000541 | 1/2005 |
| WO | WO 2005/030004 | 4/2005 |
| WO | WO 2005/039352 | 5/2005 |
| WO | WO 2005/055863 | 6/2005 |
| WO | WO 2005/058182 | 6/2005 |
| WO | WO 2005/058185 | 6/2005 |
| WO | WO 2005/058186 | 6/2005 |
| WO | WO 2005/058187 | 6/2005 |
| WO | WO 2005/063142 | 7/2005 |
| WO | WO 2005/070324 | 8/2005 |
| WO | WO 2005/072559 | 8/2005 |
| WO | WO 2005/087047 | 9/2005 |
| WO | WO 2005/092145 | 10/2005 |
| WO | WO 2005/110149 | 11/2005 |
| WO | WO 2005/120387 | 12/2005 |
| WO | WO 2005/120388 | 12/2005 |
| WO | WO 2005/120390 | 12/2005 |
| WO | WO 2005/122943 | 12/2005 |
| WO | WO 2005/122949 | 12/2005 |
| WO | WO 2005/122950 | 12/2005 |
| WO | WO 2006/019289 | 2/2006 |
| WO | WO 2006/020698 | 2/2006 |
| WO | WO 2006/028315 | 3/2006 |
| WO | WO 2006/032367 | 3/2006 |
| WO | WO 2006/041116 | 4/2006 |
| WO | WO 2006/041920 | 4/2006 |
| WO | WO 2006/060887 | 6/2006 |
| WO | WO 2006/062570 | 6/2006 |
| WO | WO 2006/066958 | 6/2006 |
| WO | WO 2006/067748 | 6/2006 |
| WO | WO 2006/067759 | 6/2006 |
| WO | WO 2006/067760 | 6/2006 |
| WO | WO 2006/082101 | 8/2006 |
| WO | WO 2006/099691 | 9/2006 |
| WO | WO 2006/099692 | 9/2006 |
| WO | WO 2006/099693 | 9/2006 |
| WO | WO 2006/099694 | 9/2006 |
| WO | WO 2006/119376 | 11/2006 |
| WO | WO 2006/120325 | 11/2006 |
| WO | WO 2007/006056 | 1/2007 |
| WO | WO 2007/008908 | 1/2007 |
| WO | WO 2007/025012 | 3/2007 |
| WO | WO 2007/049298 | 5/2007 |
| WO | WO 2007/058716 | 5/2007 |
| WO | WO 2007/064519 | 6/2007 |

* cited by examiner

ORAL CARE IMPLEMENT WITH CAVITATION SYSTEM

CROSS REFERENCE TO RELATED APPLICATIONS

This application is a continuation of U.S. application Ser. No. 12/159,279, filed Jul. 22, 2010, now allowed, which is a U.S. National Phase Entry of International Application No. PCT/US2008/065704, filed Jun. 4, 2008. The entirety of each of the foregoing applications is hereby incorporated by reference.

BACKGROUND OF THE INVENTION

The present invention pertains to an oral care implement, in particular, to a toothbrush with a cavitation system. Individuals exhibit many forms of poor oral health including tooth decay, periodontal diseases and bad breath (halitosis). Tooth decay and periodontal disease are typically caused by harmful bacteria within the mouth. When the harmful bacteria mixes with proteins present in saliva, a film of plaque is formed on the teeth and soft tissue. If the plaque is not removed, it can attack the teeth and create cavities. Additionally, the plaque will attack the soft tissue within the mouth and cause gum disease, the leading cause of tooth loss in adults. Many individuals, especially young children, do not regularly brush their teeth or perform interdental cleaning of their teeth. Such habits often can be attributed to the individual regarding tooth brushing as a mundane duty with few pleasurable aspects.

BRIEF SUMMARY OF THE INVENTION

The present invention pertains to an oral care implement with a vibratory system that may produce cavitation in oral fluid.

In one aspect, an oral care implement generates cavitation within the oral cavity. One or more cavitation cleaning elements may be located in the head area of the oral care implement. The cavitation cleaning element vibrates at a frequency that produces cavitation of fluids within the oral cavity.

In one aspect, an oral care implement includes an oral care region having cleaning elements and an elastomeric cavitation cleaning element; and a body for gripping the implement.

In one aspect, an oral care implement includes an oral care region having cleaning elements and a vibratory cleaning element configured to vibratory release an oral care substance from a container; and a body for gripping the implement. In another aspect, the vibratory cleaning element can be provided in the form a cavitation cleaning element.

Other features and advantages of the invention will become apparent from the following description taken in conjunction with the following drawings.

DETAILED DESCRIPTION OF THE INVENTION

In the following description, the invention is discussed in terms of a toothbrush (e.g. a form of an oral care implement) but could be in the form of other personal care implements. Further, it is understood that other embodiments may be utilized and structural and functional modifications may be made without departing from the scope of the present invention.

Figure 1:
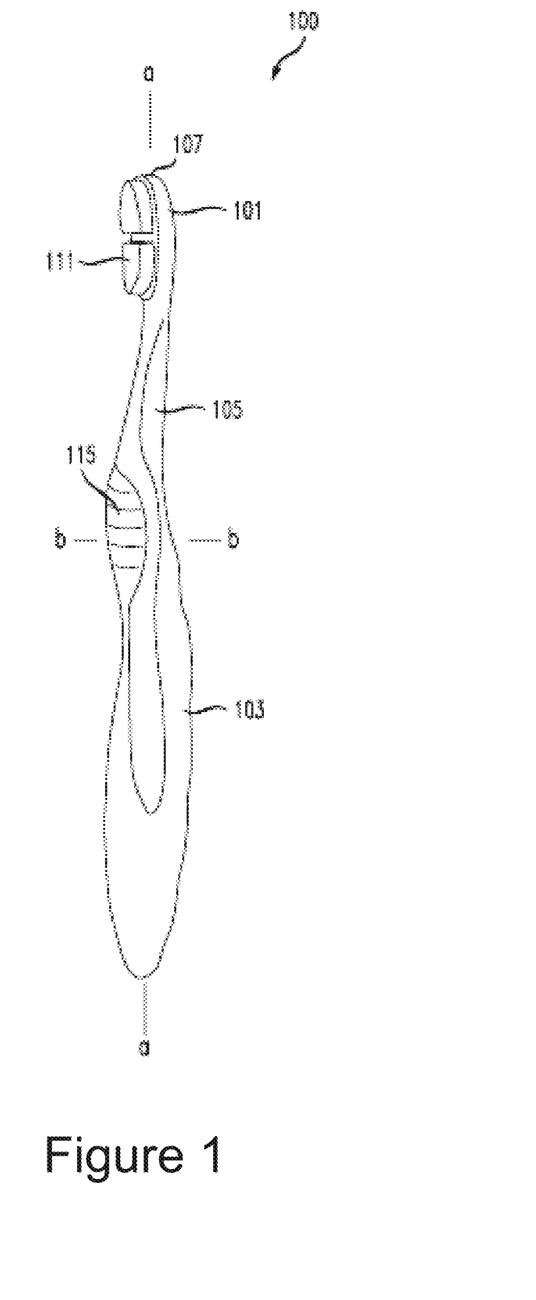
FIGS. 1 and 2 are schematic perspective front and rear views of an oral care implement, such as a toothbrush, according to one or more embodiments of the invention.
Figure 2:
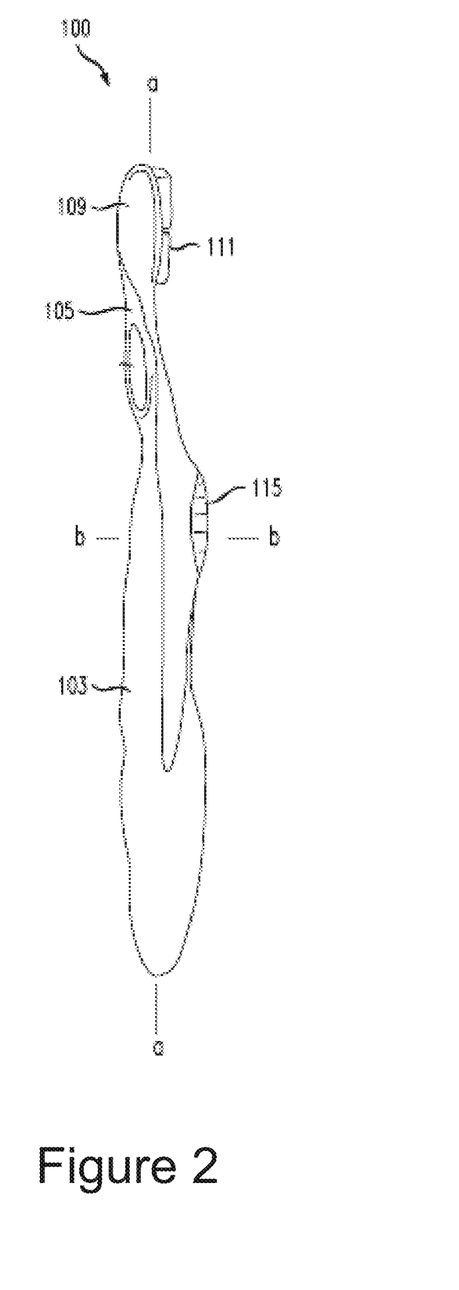
Figure 3:
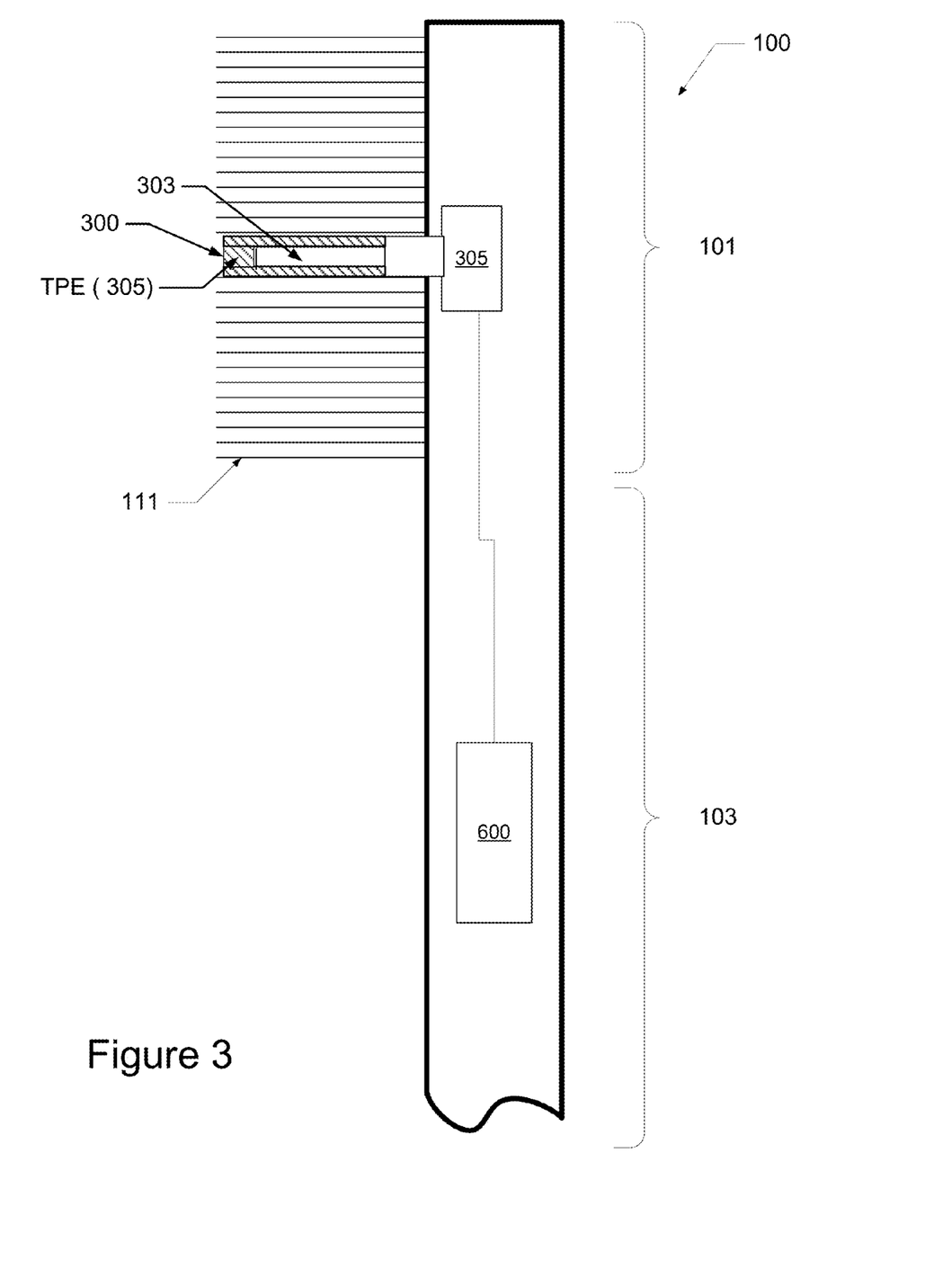
FIG. 3 is a schematic representation of the toothbrush construction according to one or more embodiments of the invention.

FIGS. 1-3 illustrate an oral care implement generally designated with the reference numeral 100. The toothbrush 100 generally includes a head 102 and a handle 103.

The handle 103 is generally an elongated body dimensioned so that a user can readily grip and manipulate the toothbrush 100. The handle 103 may be formed of many different shapes, lengths and with a variety of constructions. In one construction, the handle 103 has a neck portion 105 positioned adjacent the head 101. The neck portion 105 may be a narrowed region on the handle 103 between head 101 and the part of the handle normally gripped by the user. Nevertheless, the neck portion 101 could be the region between the head 101 and the part of the handle normally gripped by the user. In another construction, the handle 103 is integrally formed with the head 101. Other attachment configurations also are possible.

The head 101 may include an oral care region comprising one or more tooth cleaning elements 111. As used herein, the term "tooth cleaning elements" or "cleaning elements" includes any type of structure that is commonly used or is suitable for use in providing oral health benefits (e.g., tooth cleaning, tooth polishing, tooth whitening, massaging, stimulating, etc.) by making contact with portions of the teeth and gums. Such tooth cleaning elements include but are not limited to tufts of bristles that can be formed to have a number of different shapes and sizes and elastomeric cleaning members that can be formed to have a number of different shapes and sizes, or a combination of both tufts of bristles and elastomeric cleaning members.

Referring to FIG. 3, in one construction, the one or more tooth cleaning elements 111 are formed from a plurality of bristles of nylon or other material. Referring to FIGS. 1 and 2, the tooth cleaning elements 111 are bristle regions having different shapes, however, it is understood that a number of different configurations of oral care implements may be utilized. The one or more tooth cleaning elements 111 may be attached to the head 101 by known methods, such as being fit within recesses formed in the head 101 along a front portion 107 of the toothbrush 100 (FIG. 1).

Referring to FIG. 3, toothbrush 100 includes head 101 with a cavitation cleaning element 300 surrounded by other tooth cleaning elements 111. The cavitation cleaning element 300 provides one or more oral benefits such as wiping, cleaning and massaging the user's teeth and gums. The cavitation element 300 is operatively connected to a motion-producing device 305. A wide variety of motion-producing devices can be used to produce vibrations over a wide range of frequencies. Various types of vibratory devices are commercially available, such as ultrasonic and microsonic transducers. One example of a vibratory device provides frequencies in the range of about 5 to 20 kHz for acoustic cavitation. The vibration frequencies may be of different waveforms, including sinusoid, square, sawtooth and the like. Nevertheless, other values and waveforms are possible. A vibratory device may be located in head of the toothbrush. When activated, vibratory device is powered by an electric power source and controlled by microelectronics (e.g. control system 600) to induce vibrations in head of the toothbrush, such as cavitation cleaning element 300.

In some constructions, a cavitation element includes vibratory eligible material, rigid or semi rigid, polymeric, protruding though the approximate center of a given bristle tuft, which vibrates with such a frequency to produce a cavitation motion in fluids present within the oral cavity. There may be more than one cavitation generator per toothbrush, as many as one per tuft in a given toothbrush head. With continued reference to FIG. 3, the cavitation cleaning element 300 may have a composite structure which includes a stiff upright portion 303 enclosed by a compressible or soft portion 305. The stiff portion 303 is provided for axial stiffness and vibration motion transfer to the soft portion 305. As can be understood, the stiff portion 303 can be composed of a nylon material such as, a nylon marketed by Dupont under the name TYNEX. Nevertheless, other materials could be used.

The cleaning elements 111 and cavitation cleaning element 300 in toothbrush 100 may have a circular cross-sectional shape, but could have other cross-sectional shapes. The round bristles in toothbrush 100 may be composed of a nylon material. One example of a nylon material is sold by Dupont under the name of TYNEX. The diameter of the round bristles can be 0.007 inches-0.008 inches thick or have other thicknesses depending on the desired cleaning action of the bristle. The soft portion of the cavitation cleaning element can be provided with an elastomeric material. In some constructions, the elastomeric material may have a hardness property in the range of A15 to A35 Shore hardness; A20 to A30 Shore hardness; or A25 to A28 Shore hardness. (why not say Shore A from 05 to 95?) As an example, one elastomeric material is styrene-ethylene/butylene-styrene block copolymer (SEBS) manufactured by GLS Corporation. Nevertheless, SEBS (why not say thermoplastic elastomer materials?) material from other manufacturers or other materials within and outside the noted hardness range could be used.

Figure 4:
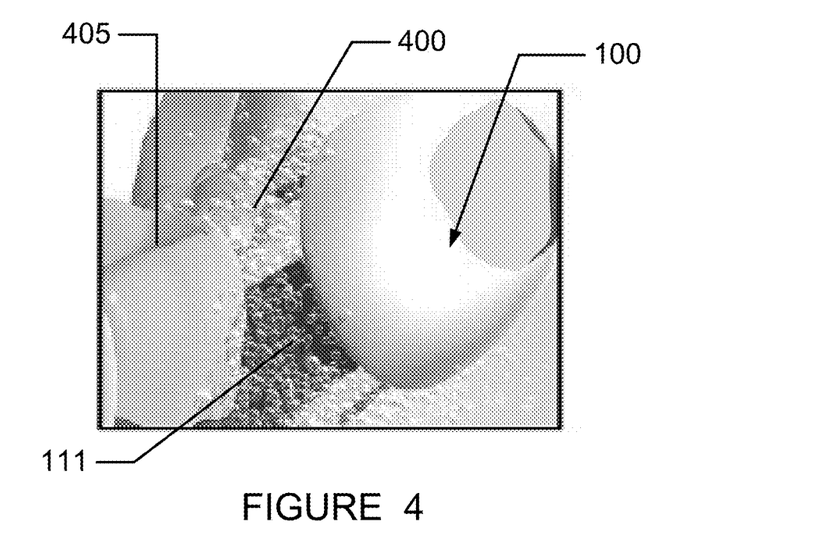
FIGS. 4 and 5 are a schematic representations of a toothbrush cleaning action in an oral cavity.
Figure 5:
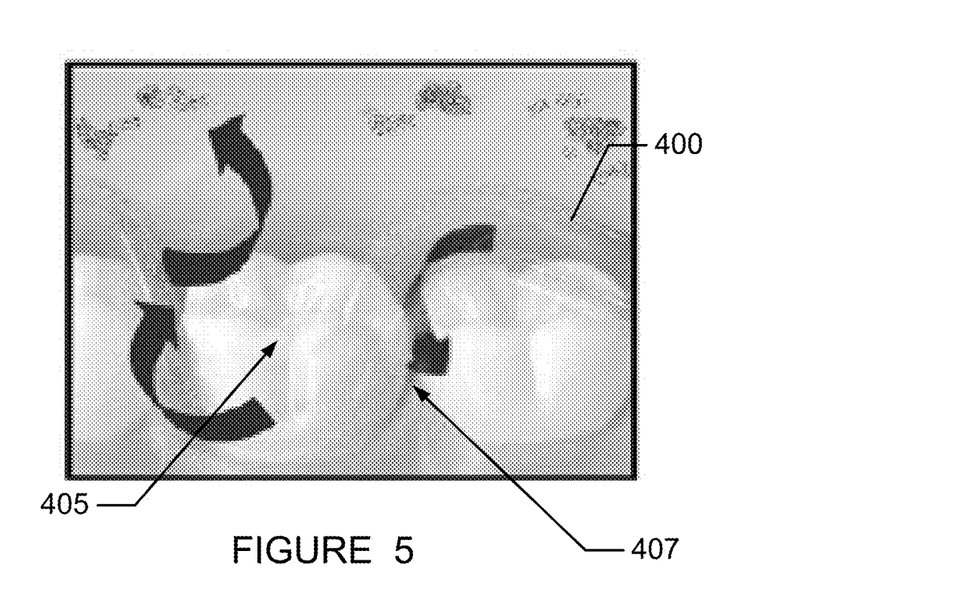

Referring to FIGS. 4 and 5, cavitation cleaning element 300 interacts with dentifrice and water within the field of cleaning elements 111. It is understood that the cavitation-dentifrice-water interaction creates a bubble matrix 400. In one aspect, the cavitation is created in the dentifrice-water fluid by ultrasonic waves. As is understood by one of skill in the art, cavitation bubbles increase and subsequently implode within a very short time. A schematic representation of bubble matrix 400 and cleaning action is shown in FIGS. 4 and 5. As can be appreciated, the bubble action generally conforms to the curvature of the teeth 405, penetrates into the interproximal areas 407 between the teeth and sweeps away the plaque and debris. The loosened plaque and debris are received by the cleaning elements 111 of the head 101. It should also be noted that the composite structure of the cavitation cleaning element 300 provides a dynamic vibratory flexing action with respect to its vertical axis, which in-turn enhances the cleaning action of the distal tip (e.g., elastomeric wiping edge) against the tooth surface.

An oral health benefit of the cavitation action within the oral cavity pertains to the enhancement toothpaste active ingredients so as to penetrate areas of the oral cavity, in particular the interproximal spaces, thus increasing the disruption of the plaque matrix. Generally, the cavitation actions increases the plaque matrix disruption normally experienced with the act of brushing one's teeth with a manual toothbrush. In addition to the increased cleaning efficacy of the cavitation action, the user may experience sensory benefits such as a cooling or heating effect, gingival stimulation, enamel polishing, soft tissue massage, or an overall increased oral cavity cleansing action.

Figure 6:
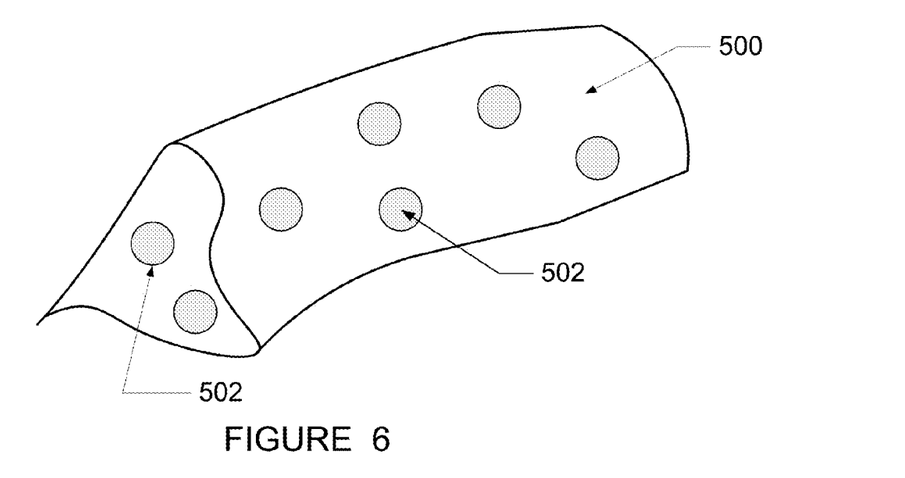
FIGS. 6 and 7 are a schematic representations of oral care materials used with an oral care implement according to one or more embodiments of the invention.
Figure 7:
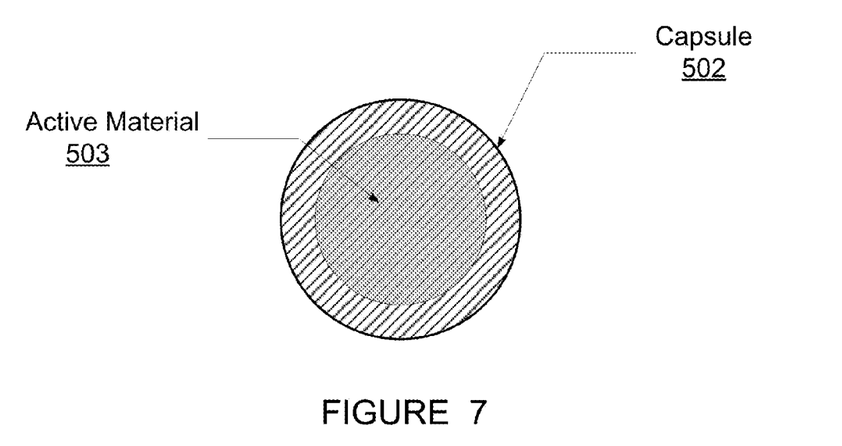

In one aspect, the toothbrush 100 has a cavitation action that provides additional benefits, and therapeutic value, in combination with specially formulated active ingredients or encapsulated active ingredients. In one construction, the toothbrush 100 has cavitation cleaning element 300 having a frequency matched to activate an oral care material (e.g., toothpaste) to provide oral care benefits. Turning to FIGS. 6 and 7, the oral care material 500 may be embedded with rupturable capsules 502 which holds and applies an oral care substance 503 (e.g., oral care solution or active material) when the walls of the capsule(s) rupture responsive to a vibration frequency. Hence, the capsules 502 can be in the form of a rupturable container having frangible, thin walls that easily rupture or burst when exposed to a "breaking frequency" of the cavitation cleaning element. In one construction, the capsule material can be made of gelatin, lactose or zeolite (hydrated aluminosilicate minerals) and with general diameters of 0.10 mm to 2 mm. The breaking frequency can be in the range of 5 kHz to 20 mHz. The materials making up capsules and the oral or mouth care solution contained therein can be consumable by the user of toothbrush 100.

The capsules 502 may include an active agent 503 within the interior void. Non-limiting examples of active agents which can be used include antibacterial agents, whitening agents, anti-sensitivity agents, anti-inflammatory agents, anti-attachment agents, plaque indicator agents, flavorants, sensates, breath freshening agents, gum health agents and colorants. Examples of these agents include metal ion agents (e.g., stannous ion agents, copper ion agents, zinc ion agents, silver ion agents) triclosan; triclosan monophosphate, chlorhexidine, alexidine, hexetidine, sanguinarine, benzalkonium chloride, salicylanilide, domiphen bromide, cetylpyridinium chloride, tetradecylpyridinium chloride, N-tetradecyl-4-ethylpyridinium chloride (TDEPC), octenidine, delmopinol, octapinol, nisin, essential oils, furanones, bacteriocins, flavans, flavinoids, folic acids, vitamins, minerals, hydrogen peroxide, urea peroxide, sodium percarbonate, PVP-H2O2, polymer-bound perxoxides, potassium nitrates, occluding agents, bioactive glass, arginine salts, arginine bicarbonate, bacalin, polyphenols, ethyl pyruvate, guanidinoethyl disulfide, tartar control agents, anti-stain ingredients, phosphate salts, polyvinylphosphonic acid, PVM/MA copolymers; enzymes, glucose oxidase, papain, ficin, ethyl lauroyl arginate, menthol, carvone, and anethole, various flavoring aldehydes, esters, and alcohols, spearmint oils, peppermint oil, wintergreen oil, sassafras oil, clove oil, sage oil, eucalyptus oil, marjoram oil, cinnamon oil, lemon oil, lime oil, grapefruit oil, and/or orange oil.

The active agent may be compatible with toothpaste, or may be unstable and/or reactive with typical toothpaste ingredients. The active agent also may be a tooth cleaning agent to boost the overall efficacy of brushing.

The active agent can be provided in any suitable vehicle, such as in aqueous solution or in the form of gel or paste. The vehicle can have a variety of different visual aesthetics including clear solution or gel or opaque solution or gel. Non-limiting examples of vehicles include water, monohydric alcohols such as ethanol, poly(ethylene oxides) such as polyethylene glycols such as PEG 2M, 5M, 7M, 14M, 23M, 45M, and 90M available from Union Carbide, carboxymethylene polymers such as Carbopol® 934 and 974 available from B.F. Goodrich, and combinations thereof. The selection of a suitable vehicle will be apparent to persons skilled in the art depending on such factors as the properties of the active agent and the desired properties of the medium, such as viscosity.

Figure 8:
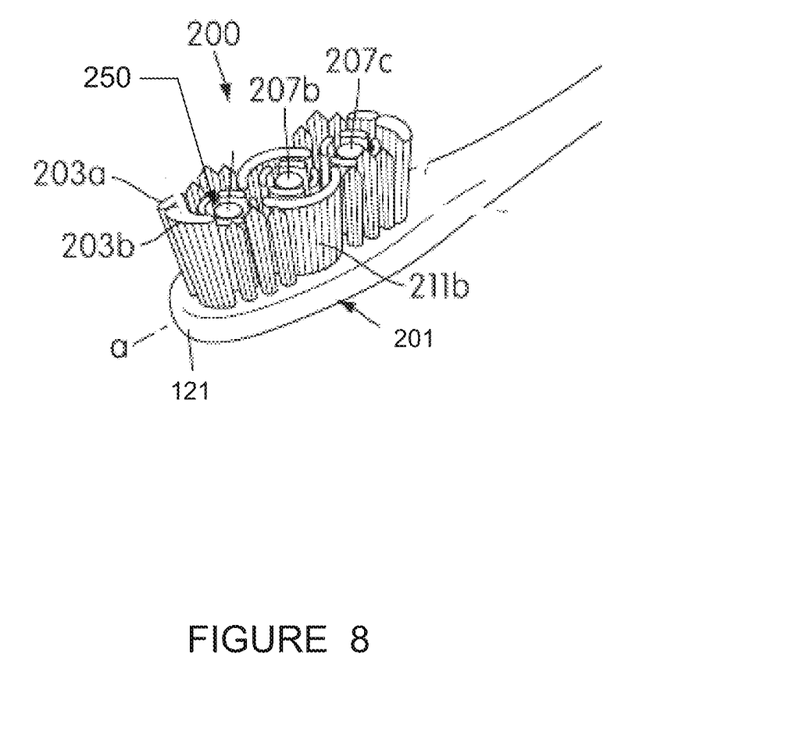
FIGS. 8 and 9 are schematic representations of a toothbrush construction according to one or more embodiments of the invention.
Figure 9:
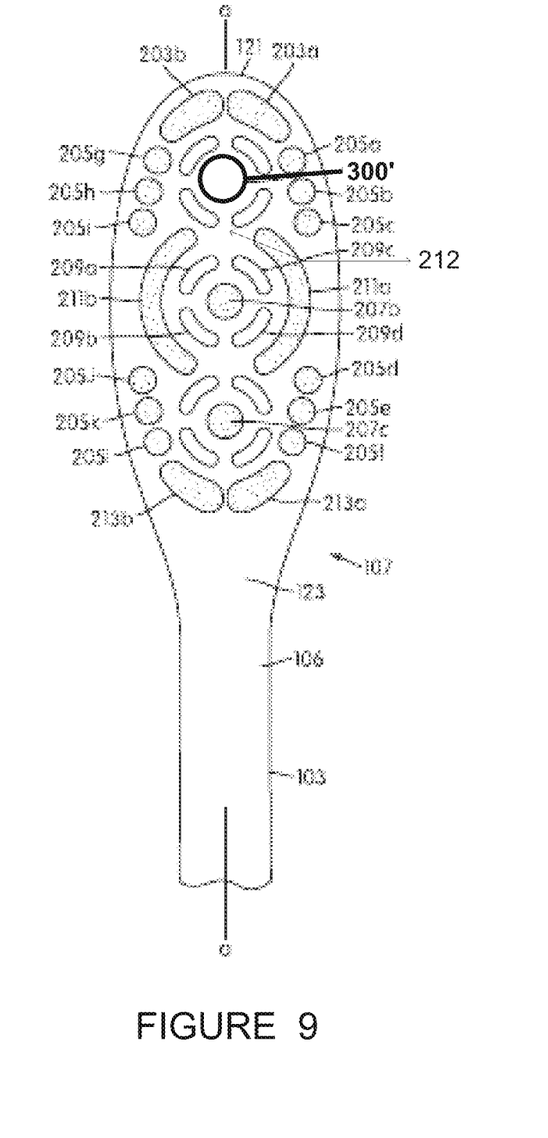

In an alternative construction of the toothbrush 200 shown in FIGS. 8-9, the tooth cleaning elements of head 201 may include a variety of tooth cleaning elements which can be used for wiping, cleaning and massaging the user's teeth and gums. In the illustrated construction of FIG. 12, tooth cleaning elements include distal tooth cleaning elements 203a-b disposed at a distal end 121 of head 201, peripheral tooth cleaning elements 205a-1, longitudinal tooth cleaning elements 207b-c disposed along longitudinal axis a-a, arcuate tooth cleaning elements 209a-d and 211a-b, and proximal cleaning elements 213a,b. Tooth cleaning elements 205, 207, 211 and 213 can be provided as tufts of bristles whereas tooth cleaning elements 209 can be formed as elastomeric walls segments. Nevertheless, other forms and types of tooth cleaning elements may be used.

In this construction, cavitation element 300' is provided generally in the center of the arcuate tooth cleaning elements structure near the distal end 121 and the distal tip of the element 300' may be disposed below the distal tips of the other elements. Nevertheless, the cavitation element 300' can be disposed at other locations on the head 201, such as generally in the center of the other arcuate tooth cleaning element structure. In this alternative construction, the cavitation generation (e.g. bubble matrix) can be driven through an isolated path to be release at or above the bristle tips. Such a structure could be molded from closed ring of bristles with uniform or irregular bristle heights, within the interior area forming a nozzle-like structure to facilitate an outlet path for the cavitation action. In the example of the arcuate elastomeric wall segments, as can be appreciated that the cavitation action can cause a dynamic vibratory flexing action of individual segments with respect to their vertical axis, which in-turn enhances the cleaning action of the distal tip (e.g., wiping edge) of the segment 209 against the tooth surface. Additionally, the interior space defined between the arcuate elements 209 forms a nozzle-like structure/configuration 250. The gaps 212 formed between the arcuate segments 209a-d enables lateral three-dimensional flow of the bubble matrix (e.g., simultaneous flows of bubbles/fluid out of the sides and vertically) to other regions of the head 101 during brushing to provide enhanced cleaning efficiency.

It should be appreciated that the nozzle-like arrangement could be formed by tightly packed, elongate bristle tufts. Further, in lieu of gaps between the elements, the nozzle configurations could have completely closed sidewall structures in other constructions. While four arcuate segment cleaning elements 209a-d are shown surrounding each of the generally cleaning elements 207, the inventive aspects may be practiced with more or fewer arcuate segments. While the arcuate segments form a generally circular structure, the segments can form an elliptical shape or a rectangular shape or other shapes in cross-section. Nevertheless, other shapes are possible to form the nozzle-like structure with various heights.

Referring to FIGS. 1 and 2, toothbrush 100 includes a front portion 107 and a rear portion 109. A thumb gripping portion 115 is provided so that a user may hold the toothbrush 100 with their thumb resting on gripping portion 115. Thumb gripping portion 115 may be formed of a pliable, cushioning material that is depressible as a user presses their thumb against it. In one or more constructions, as described herein, the thumb gripping portion 115 may serves as an actuator to control operation of the toothbrush features. For example, thumb gripping portion 115 may serve as a button to turn control a device associated with the toothbrush 100 "on" and/or "off". For example, the device may be a cavitation generator.

In one construction, thumb gripping portion 115 serves as a button to change a mode of operation of the toothbrush 100. Button 115 enables a user to change the mode of operation to any of a number of different operations. (e.g., a vibratory high or low mode). For example, depression or other engagement of button 115 may change the mode of operation to a low mode. A subsequent engagement of button 115 may change the mode of operation to a higher frequency mode. A subsequent engagement of button 115 may change the mode of operation to manual operation only. Nevertheless, the specific order of the engagement events of the button 115, does not limit the scope of the inventive concepts. It should be recognized that toothbrush 100 may have two or more buttons or actuators for controlling the modes of operation.

Figure 10:
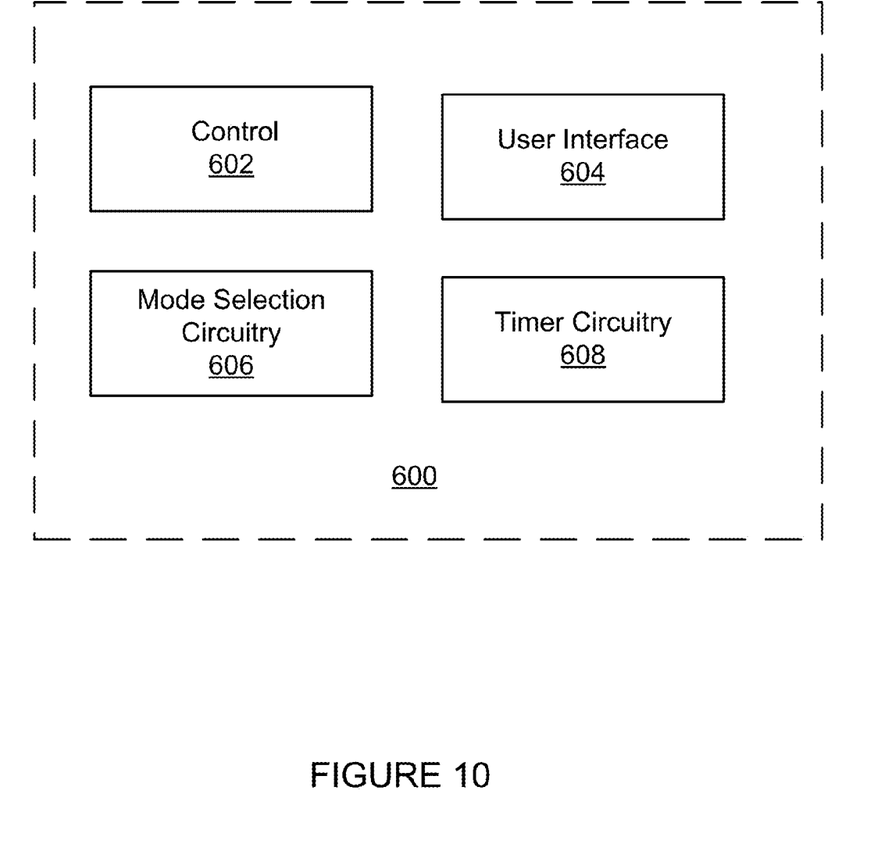
FIG. 10 is an example functional block diagram of components of a control system according to one or more embodiments of the invention.

As described herein with respect to FIG. 10, a control system 600 for toothbrush constructions 100 may be included to control vibration operation. One or more of the components shown in FIG. 10 may be included within one or more printed circuit boards. Possible alternatives include flash memory, flash ROM, RAM with battery backup. Control system 600 may include a cavitation generator control 602 operatively connected to one or more components of the system 600 and a user interface 604, such button 115.

Mode selection circuitry 606 may include electrical circuitry, software, computer-readable instructions, or other components to allow for changing the mode of operation of the toothbrush 100. Mode selection circuitry 606 may be configured to perform the functions for processing signal(s) performing computer-readable instructions, and reading from and writing to a memory (not shown) associated with the toothbrush 100 switching between different modes of operation.

Timer circuitry 608 may include hardware, software, computer-readable instructions, or other components to allow for counting up or counting down time. Timer circuitry 608 may include a crystal oscillator for counting seconds, minutes, etc. Timer circuitry 608 may be configured to perform the functions for processing signal(s) performing computer-readable instructions, and reading from and writing to a memory (not shown) associated with the toothbrush 608 operating in a timer mode for two (2) minutes. In one arrangement, the vibration mode can end after an elapsed time of two minutes.

The control system circuitry 600 may include hardware, software, computer-readable instructions, or other components to enable control of the toothbrush cavitation function. For example, the control system 600 may include memory of a programmable type in which nonvolatile storage can be electrically erased and reprogrammed.

As discussed, the inventive aspects may be practiced for a manual toothbrush or a powered toothbrush with moving tooth cleaning elements. While the various features of the toothbrush 100 work together to achieve the advantages previously described, it is recognized that individual features and sub-combinations of these features can be used to obtain some of the aforementioned advantages without the necessity to adopt all of these features.

While the invention has been described with respect to specific examples including presently preferred modes of carrying out the invention, those skilled in the art will appreciate that there are numerous variations and permutations of the above described systems and techniques. Thus, the spirit and scope of the invention should be construed broadly as set forth in the appended claims.

The following examples of a rupturable capsule are provided for illustrative purposes and should be construed as illustrative and not limiting.

EXAMPLE 1

Table I illustrates a cetylpyridinium chloride concentrate that may be dispensed from a rupturable capsule during brushing as an antibacterial agent.

TABLE I

| Ingredient | Wt % |
|---|---|
| Carbopol 974P | 1-2 |
| PEG 600 | 10 |
| FD&C blue #1(1% solution in water) | 0.5 |
| Cetylpyridinium chloride | 20 |
| Water | Q.S. |

EXAMPLE 2

Table II shows a hydrogen peroxide solution that may be dispensed from a a rupturable capsule during brushing as a whitening booster.

TABLE II

| Ingredient | Wt % |
|---|---|
| Carbopol 974P | 1-2 |
| Hydrogen peroxide | 30 |
| Water | Q.S. |

EXAMPLE 3

Table III illustrates a hydrogen peroxide gel that may be dispensed from a a rupturable capsule during brushing as a whitening liquid. The gel also may be applied post-brushing for tooth whitening.

TABLE III

| Ingredient | Wt % |
|---|---|
| Water | 10.07 |
| Carbopol 974 | 1.00 |
| 95% Ethyl alcohol | 34.8 |
| Glycerin | 5.00 |
| PEG 600 | 10.00 |
| PEG 2M | 14.00 |
| Hydrogen peroxide | 25.00 |
| 85% Phosphoric acid | 0.05 |
| Monobasic sodium phosphate | 0.05 |
| Total | 100.00 |

EXAMPLE 4

Table IV shows a phosphoric acid solution that may be dispensed from a a rupturable capsule during brushing as a whitening liquid. The solution has a pH of about 4.0.

TABLE IV

| Ingredient | Wt % |
|---|---|
| Purified water | 25.1 |
| Carbopol 974 | 1.00 |
| 95% Ethyl alcohol | 34.8 |
| Glycerin | 5.00 |
| PEG 2M | 15.00 |
| Urea peroxide | 18.00 |
| 85% Phosphoric acid | 0.10 |
| Monobasic sodium phosphate | 1.0 |
| Total | 100.00 |

EXAMPLE 5

Table V illustrates another hydrogen peroxide solution that may be dispensed from a rupturable capsule during brushing as a whitening booster. The composition alternatively may be applied to the teeth after brushing as a whitening agent.

TABLE V

| Ingredient | Wt % |
|---|---|
| Carbopol 974P | 1 |
| 95% ethyl alcohol | 34.8 |
| Glycerin | 5 |
| PEG 600 | 10 |
| PEG 2M | 14 |
| 85% phosphoric acid | 0.05 |
| Monobasic sodium phosphate | 0.05 |
| Hydrogen peroxide | 25 |
| Water | Q.S. |

EXAMPLE 6

Alternative liquid whitening gels are prepared by modifying the base formula of Example 5 by adding either (1) 2 to 5 wt % polyethylene (PE) powder having an average particle size of 6 to 8 microns; (2) 1 to 5 wt % polytetrafluoroethylene (PTFE) powder having particle size of 5 to 6 microns; (3) 0.8 to 2.5 wt % polypropylene (PP) powder having a particle size of 4 to 50 microns; (4) 2 to 5 wt % PE powder and 0.11 to 0.4 wt % titanium dioxide powder having a particle size of 10 to 45 microns. Examples of gels having the polymer and/or inorganic titanium powders incorporated in the base formula are shown in Tables VI and VII.

TABLE VI

| | A (wt %) | B (wt %) | C (wt %) | D (wt %) | E (wt %) | F (wt %) | G (wt %) |
|---|---|---|---|---|---|---|---|
| Base Formula | 99.0 | 98.0 | 95.0 | 98.0 | 95.0 | 99.2 | 97.5 |
| +PE | — | — | — | 2.0 | 5.0 | — | — |

TABLE VI-continued

| | A (wt %) | B (wt %) | C (wt %) | D (wt %) | E (wt %) | F (wt %) | G (wt %) |
|---|---|---|---|---|---|---|---|
| +PTFE | 1.00 | 2.0 | 5.0 | — | — | — | — |
| +PP | — | — | — | — | — | 0.8 | 2.5 |

TABLE VII

| | GA (wt %) | H (wt %) | I (wt %) | J (wt %) | K (wt %) | L (wt %) |
|---|---|---|---|---|---|---|
| Base Formula | 99.5 | 97.90 | 97.80 | 97.60 | 94.90 | 99.5 |
| +PE | — | 2.00 | 2.00 | 2.00 | 5.00 | — |
| +TiO$_2$ | — | 0.10 | 0.20 | 0.40 | 0.10 | 0.5 |
| +TiO$_2$ coated mica | 0.5 | — | — | — | — | — |

EXAMPLE 7

Table VIII shows another exemplary composition of a liquid whitening gel that may be dispensed from a rupturable capsule during brushing as described herein.

TABLE VIII

| Liquid Gel Formula | Wt % |
|---|---|
| Carbomer | 1.00 |
| PEG 600 | 9.96 |
| BHT | 0.03 |
| Glycerin | 4.98 |
| Water | 17.00 |
| Ethyl alcohol | 34.67 |
| PEG 2M | 13.95 |
| H$_2$O$_2$ (35%) | 17.93 |
| Sodium Phosphate | 0.05 |
| Phosphoric acid | 0.05 |
| Titanium dioxide | 0.38 |

EXAMPLE 8

Table IX example shows the composition of a breath protection gel that is dispensed from a rupturable capsule as described herein.

TABLE IX

| Ingredient | Wt % |
|---|---|
| Carbopol 974P | 1 |
| PVM/MA copolymer | 10 |
| Triclosan | 20 |
| Ethyl alcohol | 40 |
| Zinc gluconate | 20 |
| Water | Q.S. |

What is claimed is:

1. An oral care system comprising:
an oral care implement comprising:
a handle;
a head attached to the handle and defining an oral care region, the oral care region further comprising:
at least one vibratory cavitation cleaning element operably connected to a motion-producing device that vibrates the vibratory cavitation cleaning element at a predetermined breaking frequency; and
an oral care substance comprising at least one rupturable capsule containing an oral care active agent, the capsule being formed with frangible thin walls and configured to rupture at the predetermined breaking frequency; and
wherein the capsule ruptures to release the active agent when the vibratory cavitation cleaning element vibrates at the predetermined breaking frequency.

2. The oral care system of claim 1, wherein the predetermined breaking frequency is selected to further cause the vibratory cavitation cleaning element to interact with the oral care substance and fluid in the oral care region to produce an imploding bubble matrix that loosens foreign matter from a user's teeth.

3. The oral care system of claim 2, wherein the vibratory cavitation cleaning element is disposed in the center of and spaced inward from arcuate stationary cleaning elements forming an interior space, the arcuate stationary cleaning elements defining a nozzle that produces a flow of a bubble matrix containing the active agent outwards from the nozzle.

4. The oral care system of claim 3, wherein the arcuate stationary cleaning elements are formed from elastomeric wall segments.

5. The oral care system of claim 3, wherein the arcuate stationary cleaning elements have gaps formed therebetween to provide lateral three-dimensional flow of the bubble matrix outwards from the nozzle to other portions of the oral care region.

6. The oral care system of claim 1, wherein the rupturable capsule is formed of a material selected from the group consisting of gelative, lactose, and zeolite.

7. The oral care system of claim 1, wherein the active agent is selected from the group consisting of antibacterial agents, whitening agents, anti-sensitivity agents, anti-inflammatory agents, anti-attachment agents, plaque indicator agents, flavorants, sensates, breath freshening agents, gum health agents and colorants.

8. The oral care system of claim 1, wherein the active agent is contained in a vehicle disposed in the capsule that is selected from the group consisting of an aqueous solution, a gel, or a paste.

9. The oral care system of claim 1 further comprising a plurality of the rupturable capsules.

10. The oral care system of claim 1, wherein the active agent is selected from the group consisting of antibacterial agents; oxidative or whitening agents; enamel strengthening or repair agents; tooth erosion preventing agents; tooth sensitivity ingredients; gum health actives; nutritional ingredients; tartar control or anti-stain ingredients; enzymes; sensate ingredients; flavors or flavor ingredients; breath freshening ingredients; oral malodor reducing agents; anti-attachment agents or sealants; diagnostic solutions; occluding agents, dry mouth relief ingredients; catalysts to enhance the activity of any of these agents; colorants or aesthetic ingredients; and combinations thereof.

11. The oral care system of claim 1, wherein the active agent is selected from the group consisting of (i) an antibacterial agent selected from the group consisting of chlorhexidine, cetyl pyridinium chloride, triclosan, stannous compounds, herbal extracts, and zinc compounds; (ii) an oxidizing or whitening agent selected from the group consisting of hydrogen peroxide, urea peroxide, sodium percarbonate, and $PVP-H_2O_2$; (iii) a gum health active selected from the group consisting of polyphenols, herbal extracts, and triclosan; (iv) a nutritional ingredient selected from the group consisting of vitamins, minerals, amino acids, vitamin E, and folic acid; (v) tartar control or anti-stain agent selected from the group consisting of phosphate salts, polyvinylphosphonic acid, and PVM/MA copolymer; (vi) a flavor or flavor ingredient selected from the group consisting of menthol, carvone, anethole, aldehydes, esters, alcohols, and oils of spearmint, peppermint, wintergreen, *sassafras*, clove, sage, *eucalyptus*, marjoram, cinnamon, lemon, lime, grapefruit, or orange; (vii) an occluding agent selected from the group consisting of sodium silicate, bioactive glass and arginine salts; (viii) an anti-attachment agent selected from the group consisting of ethyl lauroyl arginate and silicone polymers; and (ix) combinations thereof.

12. The oral care system of claim 1, wherein the cavitation cleaning element is configured for operation for a predetermined elapsed period of time.

\* \* \* \* \*